Figure 1:
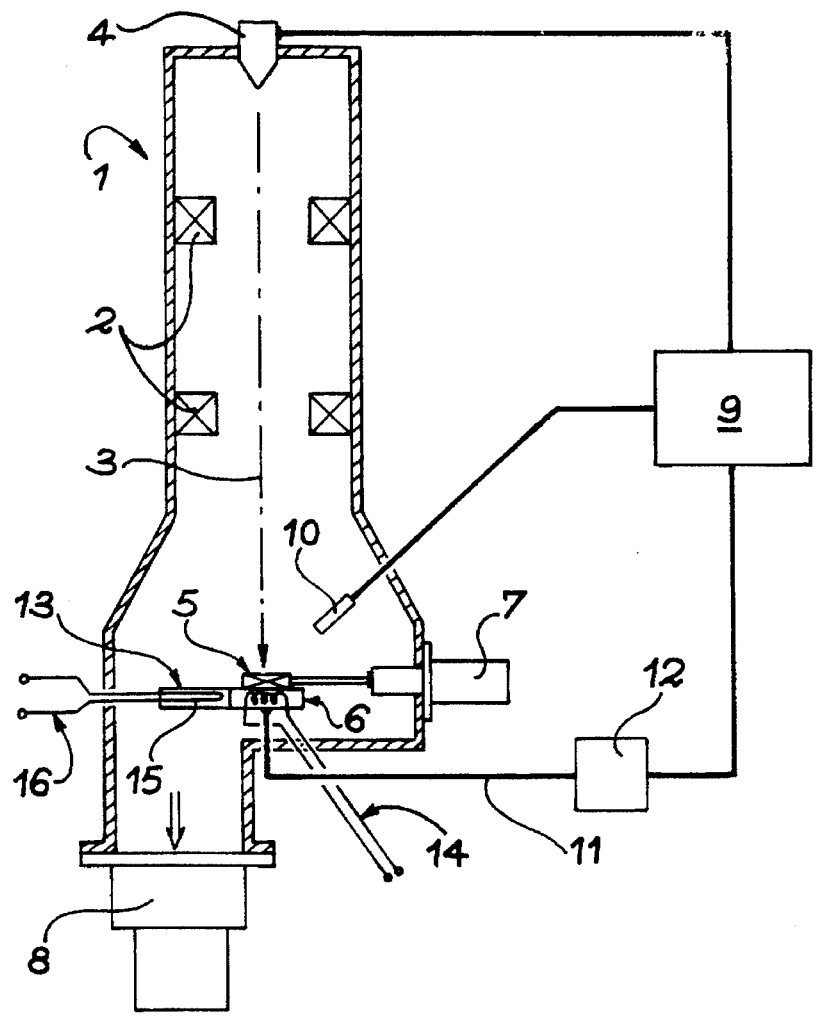

United States Patent [19]

Le Gressus et al.

[11] Patent Number: 5,635,715
[45] Date of Patent: Jun. 3, 1997

[54] PROCESS FOR THE CHARACTERIZATION OF AN INSULATOR AND THE CORRESPONDING ELECTRON MICROSCOPE

[75] Inventors: Claude Le Gressus, Fontenay-le-Fleury; Claude Faure, Lesigny; Daniel Acroute, Marck; Jose Bezille, Dunkerque; Hakim Janah, Bleriot/Plage; Gerard Moya, Plan-de-Cuques; Guy Blaise, Clichy, all of France

[73] Assignees: A L'Energie Atomique, Paris; Alcatel Cables, Clichy Cedex, both of France

[21] Appl. No.: 448,376

[22] PCT Filed: Oct. 7, 1994

[86] PCT No.: PCT/FR94/01172

§ 371 Date: Jun. 18, 1996

§ 102(e) Date: Jun. 18, 1996

[87] PCT Pub. No.: WO95/10784

PCT Pub. Date: Apr. 20, 1995

[30] Foreign Application Priority Data

Oct. 8, 1993 [FR] France .................. 93 12019

[51] Int. Cl.$^6$ .................. G01R 31/12; G01N 27/92; H01J 37/256
[52] U.S. Cl. .................. 250/307; 250/310
[58] Field of Search .................. 250/307, 310

[56] References Cited

U.S. PATENT DOCUMENTS

| 5,432,345 | 7/1995 | Kelly | 250/307 |
| 5,512,746 | 4/1996 | Saito | 250/310 |

FOREIGN PATENT DOCUMENTS

| 4020806 | 1/1991 | Germany . | |
| 52-42789 | 4/1977 | Japan | 250/307 |
| 0060337 | 9/1982 | WIPO . | |

OTHER PUBLICATIONS

Patent Abstracts of Japan; vol. 8, No. 51; p. 259; Mar. 8, 1994.
Journal of Applied Physics; vol. 69, No. 9, pp. 6334–6339, May 9, 1991; G. Blaise et al.; Charging and Flashover Induced By Surface Polarization Relaxation Process.
International Search Report; PCT/FR94/01172; Jan. 25, 1995; Falk Heck.

*Primary Examiner*—Jack I. Berman
*Attorney, Agent, or Firm*—Fish & Richardson P.C.

[57] ABSTRACT

Process and apparatus for the characterization of an insulator (5) at breakdown with the aid of an electron microscope (1), in which the electron flow rate of the beam (3) is adjusted as a function of in particular backscattered, lost, secondary or absorbed electrons. An automatic controller (9) sensitive to certain sensors (10,12) is provided for this purpose. The electron flow rate is proportional to the voltage to be simulated in the insulator.

5 Claims, 1 Drawing Sheet

PROCESS FOR THE CHARACTERIZATION OF AN INSULATOR AND THE CORRESPONDING ELECTRON MICROSCOPE

DESCRIPTION

The invention relates to a process for the characterization of an insulator and to a corresponding electron microscope.

EP-A-470,910 refers to an electron microscope usable for this purpose, firstly by implanting electric charges at the surface of the insulator and then measuring the positions of the equipotentials, which are normally circular and concentric curves at the implantation point. For this purpose the electron beam is displaced to the surface of the sample once the electric charges have been implanted, its potential being regulated to the value of the sought equipotential and a specular method is applied, whose criterion is that a transition between the absorption and the reflection of the beam is marked on arriving at the equipotential. This process makes it possible to plot a function expressing the evolution of the electric potential at the surface of the sample as a function of the inverse of the radius or the distance at the charge implantation point. This function, which in principle has a useful straight part, gives an estimate of the dielectric characteristics of the insulator and its breakdown strength simply through the gradient of the line, because the potential measured on a good insulator decreases very rapidly with the distance at the implantation point and the charges are virtually unable to move. However, this method is only valid under quasi-static conditions. However, it is well known that the resistance or strength of the insulator can be very different if a periodic, variable voltage or an isolated pulse is applied. It is then necessary to examine known characterization methods under such conditions. According to the conventional method, the samples are subject to the test voltage by electrodes and an inspection is made to establish if a breakdown has occurred. However, the disadvantage; which also applies in statics, is that the result measured is effectively not only dependent on the characteristics of the actual insulator, but also on the quality of its contact with the electrodes. Significant precautions have to be taken in order to protect the exterior of the location where the experiment is performed, because the voltages are often extremely high.

Improvements which have already been proposed by which the electric potential is created by a heat or pressure wave, which is possible with certain materials, still suffer from the disadvantage that electrodes are required for measuring the response of the insulator. These methods are also more difficult to use.

The invention is based on the finding that a satisfactory modelling of transient voltage conditions can also be obtained by using a scanning electron microscope provided that certain measures are taken, because the influence of certain phenomena are noticed whereas it would be imperceptible under static conditions.

Thus, account must be taken of the last electron flow rates for the implantation on the surface of the sample, i.e. mainly reflected electrons, more specifically be backscattering, as well as secondary electrons and electrons absorbed by the sample, but which escape therefrom.

Therefore the invention relates to a process making it possible to surmount these difficulties and perfectly simulate the placing under voltage in scanning electron microscopes. An ancillary problem which is solved is to virtually simultaneously subject the sample to calorific measurements without dismantling or displacing it.

It has in fact been found that calorific capacity variations of the sample brought about by the injection of charges make it possible to indicate if its behaviour would or would not deteriorate on aging, which is very important for buried electric cables, whose life must be very long.

The invention consequently relates to a process for the characterization of an insulator on breakdown using a scanning electron microscope by which electrons of a beam are injected at one location of the insulator, then the beam is moved in front of the insulator to measure the electric potential on the insulator at certain distances from the injection location, said process being characterized in that it includes a measurement of the flow rates of electrons reflected from the insulator and an adjustment of the flow rate of the beam as a function of said reflected electron flow rate using an automatic controller for injecting a given flow rate of electrons which are not reflected, in accordance with a given time function. The time function is preferably identical to the time voltage of an electric voltage to be simulated on the insulator, to within a proportionality coefficient. Finally, it is advantageous for the process to include calorific capacity measurements with respect to the insulator before or after injection by placing it on a calorimeter positioned in the microscope.

It also relates to an electron microscope for performing this process and which includes means for measuring the flow rates of electrons reflected from the sample and for adjusting the electron beam flow rate as a function of said reflected rates in order to obtain a flow rate of electrons which are not reflected or returned. According to the invention, it is used for implanting electric charges at a fixed point of the sample in accordance with a giventime function, unlike in the prior art of DE-A-4,020,806, which relates to an electron microscope, whose electron flow rate is dependent on the flow rate of secondary electrons so as not to burden the sample. This process is only useful for a conventional utilization of the microscope on observing a sample scanned by a mobile beam, which encounters insulating zones, which must not be charged because otherwise an excessive brightness would be obtained, because the electrons are only slightly diffused and remain substantially in situ. Thus, it is preferable to reduce the incident electron flow rate.

The invention is described in greater detail hereinafter relative to non-limitative embodiments and the attached drawings, wherein show:

FIG. 1 a view of an apparatus for performing the invention.

Figure 2:
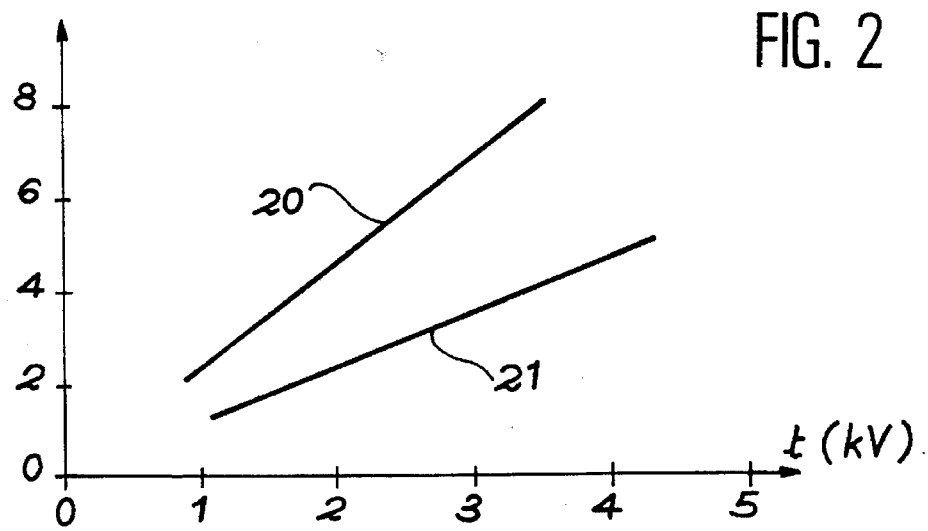

FIG. 2 an example of the results obtained.

FIG. 1 shows an electron microscope 1, which in the usual way incorporates magnetic means 2 for directing and accelerating an electron beam 3 emitted by an electron gun 4 at the top of the column of the electron microscope 1. The sample 5 is placed on a support 6 and is mobile under the action of means such as a push rod /, to which it is connected by not shown means enabling it to also be pulled. Thus, it is possible to vary the electron impact point on the sample 5.

A vacuum pump 8 makes it possible to suck up the gaseous content at the electron microscope 1. An automatic controller 9 adjusts the electron flow mate of the beam 3. It makes use of a detector for secondary and backscattered electrons 10, oriented towards the sample 5, as well as an absorbed current measuring circuit 11 connected to the support 6 and provided with an ammeter 12 or an equivalent means. The detector 10 and the circuit II are both connected to the automatic controller 9, whose function is to add to the initially provided electron flow rate a supplementary rate equal to the sum of the rates corresponding to the secondary, backscattered and absorbed electrons. Thus, a perfectly controlled electron flow rate is injected at a fixed point of the sample 5 and stays there.

This flow rate is proportional to the voltage which it is wished to simulate and consequently corresponds to a signal of the same form (sinusoidal, square, pulse-type, etc.) and of the same frequency or duration. The sampling step of the signal, corresponding to the reaction time of the automatic controller 9, is a few microseconds with known electron systems or even much less, which is sufficient for supplying perfect or almost perfect simulations for ordinary situations.

When the simulation signal is completely supplied, use is again made of the known method for estimating the dielectric qualities of the sample 5, involving the displacement of the electron beam 3 after raising it to an electric potential which is different on each occasion, in order to measure the distance between the impact point and the equipotential on the sample 5 at the sample potential as the electron beam 3, as a result of the transition between the reflection and the absorption of the electron beam 3, which then appears. The curves of FIG. 2 give voltages on the abscissa and inverses of the distance (or the radius of the equipotential) on the ordinate, expressed in arbitrary units. Curve 20 is representative of a continuous signal and curve 21 of a signal formed from pulses lasting two microseconds. As curve 21 has a smaller gradient, it can be deduced that the flow of the charges at the surface of the sample 5 is more pronounced when the charge is applied in a continuous manner and that therefore the breakdown resistance of the insulator is interior.

The electric potential of the electron beam 3 is freely chosen during the implantation of the charges and can in practice be 30 to 40 kV.

The electron microscope 1 finally incorporates a Calvet microcalorimeter 13 and heating or cooling means 14 located in the support 6 and whose function is to be heat or cool the sample 5 by the Joule or Peltier effect. They can be constituted by a heating coil in the first case, which brushes the sample 5, or a pair of electrodes in the second case, whereof one touchs the sample 5 and the other is enveloped in the support 6.

The means 14 and the microcalorimeter 13 enable the performance of measurements of the specific heat of the insulator. If this heat decreases following the injection of the charges, it is deduced therefrom that there is a rearrangement of the internal energy at the sample 5 and it can be assumed that it will not or will only scarcely age in time, i.e. its breakdown characteristics will not deteriorate. The measurement is made possible by sliding the sample 5 from the upper surface of the support 6 to that of the microcalorimeter 13, which is continuous therewith. It is pointed out that the vacuum is established in the microscope 1, which eliminates convection-based heat losses. It is consequently possible to modify a conventional microcalorimeter, where the sample would be installed in a closed cavity, by placing the measuring means (a thermopile in the case of a Calvet microcalorimeter) on the upper surface of the apparatus. The thermopile is then sensitive to the temperature difference between the sample 5 placed thereon and the remainder of the apparatus. It carries the reference 15 in FIG. 1 and the electric wires by which the current flows expressing the temperature difference are designated 16,

We claim:

1. Process for the characterization of an insulator (5) at breakdown using a scanning electron microscope (1) by which electrons of a beam (3) are injected at one location of the insulator, then the beam is moved in front of the insulator to measure the electric potential on the insulator at certain distances from the injection point, characterized in that the process involves a measurement (9) of the flow rates of electrons reflected by the insulator and an adjustment of the flow rate of the beam as a function of said flow rate of reflected electrons by an automatic controller in order to inject a given flow rate of electrons which are not reflected, in accordance with a given time function.

2. Process for the characterization of an insulator on breakdown according to claim 1, characterized in that the time function of the electron flow rate is identical to the time function of as electric voltage to be simulated on the insulator, to within a proportionality coefficient.

3. Process for the characterization of an insulator on breakdown according to claim 1, characterized in that it involves measurements of the calorific capacity of the insulator before or after injection by placing it on a calorimeter (13) located in the microscope (1).

4. Scanning electron microscope (1), comprising an electron beam (3) projected onto a sample (5), having means (9) for measuring the flow rates of electrons reflected from the sample (5) and for adjusting the flow rate of the electron beam (3) as a function of said reflected flow rates in order to obtain a flow rate of electrons which are not reflected, characterized in that it is used for implanting electric charges on a fixed point of the sample in accordance with a given time function.

5. Scanning electron microscope according to claim 4, characterized in that it contains a calorimeter (13).

* * * * *